(12) United States Patent
Wei (10) Patent No.: US 10,049,189 B2
(45) Date of Patent: Aug. 14, 2018

(54) METHOD FOR DEVELOPING PARENTERAL THERAPEUTIC PRODUCT WITH DRUG DELIVERY DEVICE THROUGH CLINICAL TRIAL

(71) Applicant: Min Wei, Carmel, IN (US)

(72) Inventor: Min Wei, Carmel, IN (US)

(73) Assignee: Min Wei, Carmel, IN (US)

( * ) Notice: Subject to any disclaimer, the term of this patent is extended or adjusted under 35 U.S.C. 154(b) by 240 days.

(21) Appl. No.: 14/859,296

(22) Filed: Sep. 19, 2015

(65) Prior Publication Data
US 2016/0092659 A1    Mar. 31, 2016

Related U.S. Application Data

(60) Provisional application No. 62/056,635, filed on Sep. 29, 2014.

(51) Int. Cl.
| | |
|---|---|
| G06Q 10/00 | (2012.01) |
| G06Q 50/00 | (2012.01) |
| G06F 19/00 | (2018.01) |
| G16H 10/20 | (2018.01) |
| A61M 5/142 | (2006.01) |
| A61M 5/145 | (2006.01) |
| A61M 5/20 | (2006.01) |
| A61M 5/24 | (2006.01) |
| A61M 5/315 | (2006.01) |

(52) U.S. Cl.
CPC .......... *G06F 19/363* (2013.01); *A61M 5/142* (2013.01); *A61M 5/14526* (2013.01); *G06F 19/3456* (2013.01); *G16H 10/20* (2018.01); *A61M 5/2033* (2013.01); *A61M 5/24* (2013.01); *A61M 5/31553* (2013.01); *A61M 5/31563* (2013.01); *A61M 2005/14513* (2013.01); *A61M 2005/206* (2013.01); *A61M 2205/702* (2013.01)

(58) Field of Classification Search
CPC ...................................................... A61M 5/142
See application file for complete search history.

(56) References Cited

U.S. PATENT DOCUMENTS

| | | | |
|---|---|---|---|
| 5,743,889 A * | 4/1998 | Sams ................ | A61M 5/31551 604/207 |
| 9,686,976 B2 * | 6/2017 | Ramsdell ............ | A01M 25/006 |

(Continued)

OTHER PUBLICATIONS

PennState Eberly College of Science. Considerations for Dose Finding Studies. Available at https://onlinecourses.science.psu.edu/stat509/node/35 as of Aug. 28, 2007.*

(Continued)

*Primary Examiner* — Kristen Matter
(74) *Attorney, Agent, or Firm* — Min Wei (57) ABSTRACT

The method set out herein involves conducting clinical trial to develop parenteral therapeutic product with drug delivery device. The method comprises conducting a dose-finding clinical study using a variable dose drug delivery device to evaluate multiple clinical doses, wherein the variable dose drug delivery device is automatic, portable and for user self-administration. During the dose-finding clinical study, both the performance of the drug and the performance of the variable dose drug delivery device are evaluated.

1 Claim, 12 Drawing Sheets

(56) References Cited

U.S. PATENT DOCUMENTS

| | | | | |
|---|---|---|---|---|
| 2010/0114038 A1* | 5/2010 | Sams | ............... | A61M 5/2033 |
| | | | | 604/211 |
| 2010/0160894 A1* | 6/2010 | Julian | ............... | A61M 5/2033 |
| | | | | 604/506 |
| 2013/0150803 A1* | 6/2013 | Shetty | ............... | A61M 5/31528 |
| | | | | 604/211 |

OTHER PUBLICATIONS

First Clinical Research Best Practices Journal. IRB Review of Human Factors/Usability Testing. Available at https://firstclinical.com/fda-gcp/?show=2012/FW_%20RESPONSE_%20IRB%20Review%20of%20Human%20Factors_Usability%20Testing&format=fulllist as of Sep. 4, 2012.*

Katz, Russell. FDA: Evidentiary Standards for Drug Development and Approval. NeuroRx, vol. 1, No. 3 (2004).*

The FDA's Drug Review Process: Ensuring Drugs are Safe and Effective. Available at https://www.fda.gov/drugs/resourcesforyou/consumers/ucm143534.htm. Last updated Nov. 6, 2014.*

* cited by examiner

METHOD FOR DEVELOPING PARENTERAL THERAPEUTIC PRODUCT WITH DRUG DELIVERY DEVICE THROUGH CLINICAL TRIAL

CROSS-REFERENCE TO RELATED APPLICATIONS

This application claims the benefit of U.S. Provisional Application Ser. No. 62/056,635, filed Sep. 29, 2014

BACKGROUND OF THE INVENTION

Currently, biologic drugs account for more than half of all therapeutic drug candidates in pharmaceutical development pipelines. These biologic drugs need to be delivered through the parenteral route. As the parenteral therapeutic drugs become more and more popular, portable automatic medication injection or infusion devices for self-administration are expected to be widely used together with the parenteral therapeutic drugs (also referred as combination products). In clinical trials, using the automatic medication injection or infusion devices can have apparent advantages over using manual syringe. For example, when using manual syringe, the manual injection force difference between the low concentration formulation (or placebo) and the high concentration formulation can be sensed by user, and therefore, the blinding effect for clinical trial will be diminished. In contrast, the user won't feel this difference if using the automatic medication injection or infusion devices because the injection/infusion forces of these devices are provided by device internal driving mechanisms. Meantime, these automatic drug delivery devices often can deliver drug more precisely than manual device.

Clinical trials of new drugs provide critical data on the drug's effectiveness, dosage requirements and possible adverse side effects. Unlike marketing strategies developed and applied to the introduction and sales of a new drug, it is desired and sometimes necessary in clinical studies to conceal or "blind" the drug to be studied. Blinding the clinical study is believed necessary to prevent bias from the participants—patients, investigators and sponsors—from comprising the results. Blinded studies can also enhance marketability of a product by more credibly demonstrating the favorable health and economic advantages, such as greater therapeutic efficacy and fewer adverse effects, when compared with a marketed drug or placebo. In addition, many governments require blinded clinical studies for approval of a new drug. (See 21 C.F.R. 314.26 and European Union's Directive 91/507/EEC). Effective blinding requires each aspect of the treatment—dosage form, packaging, labeling, dosage interval, dosage strength and dosage composition—to appear the same. That is, none of the participants to the study should be able to discern whether they are taking placebo, one or more strengths of investigational drug, or one or more strengths of comparator drug (the comparator or control drug is a marketed drug commonly used for the disease being studied). The blinding procedure is further complicated by the need to comply with all aspects of Good Manufacturing Practices (GMP) requirements.

Autoinjector or infusor devices, as the most used automatic drug delivery devices for self-administering parenteral therapeutic drugs, are mostly designed for fix dose delivery. This presents following challenge to be used for clinical trial: difficult to conduct clinical trial when different doses are evaluated, for example, during the dose-finding clinical study. This challenge often delays the introduction of auto- injector or infusor device to clinical trial until the final dose is determined. Clinical trial is the most time consuming and most expensive part of drug development. Normally, all the three phases clinical trial together can take 5-8 years and cost hundreds of million dollars. During the long time period and with the substantial spending, there are a lot of learning about the drug, for example, how the drug is absorbed, metabolized, and what the drug effect look like. On the other hand, when the parenteral therapeutic drug is developed together with the drug delivery device, there isn't much learning about the delivery device in the early phases of clinical trial, especially human factor and usability of the device, which is highly recommended by Food and Drug Administration (FDA) (FDA draft guidance—Applying Human Factors and Usability Engineering to Optimize Medical Device Design, 2011). As mentioned above, in phase I and phase II clinical trials, a very important aspect is dose-finding, which requires devices that can deliver variable dose. Therefore, the current fixed dose drug delivery device is often introduced during very late stage of clinical trial. In contrast, for oral drugs, the dose forms are being optimized throughout the all phases of the clinical trial period. Currently, the clinical trial for parenteral therapeutic drug start with vial/manual syringe combination. Until phase III, the more sophisticated device, such as autoinjector or infusor will be introduced and studied. Or, the more sophisticated device will be evaluated after the first launch of the drug in vial/manual syringe format. As the results, drug developers not only under-utilize the advantage of using autoinjector or infusor device in clinical trials, but also lose the opportunity to test device human factors and usabilities during the clinical trials.

In summary, what is needed is a new method for conducting blinded clinical studies which permits for improved development of parenteral therapeutic products with automatic drug delivery device during clinical trials.

SUMMARY OF THE INVENTION

Generally speaking, there is provided a method for improved use of automatic drug delivery device during the clinical trials for developing parenteral therapeutic products. The method includes using portable variable dose drug delivery device for self-administration as early as in first-in-human clinical trial (Phase I), then using the variable dose drug delivery device for dose-finding clinical study (Phase II). When it gets to phase III, the variable dose drug delivery device or corresponding fixed dose drug delivery device can be used for final product evaluation. All the automatic drug delivery devices presented here use pre-filled medication container for formulation in fluid state. Because the pre-filled dose form is easier to use for all people (much simpler preparation procedure and require less amount of professional training), including medical professionals who conducting clinical trials, there is no need to use the traditional lyophilized powder in vial unless the drug is unstable in the fluid formulation. Actually, one major reason to use vial/syringe format is for clinical researchers to be able to adjust injection dose. With the variable dose drug delivery, it not only makes the randomization and blinding and clinical trial design become easier, but also simplify the clinical trial manufacturing because there is no need to produce too many drug formulations. It can be expected that large amount of resources can be saved with using the new method invented here. Moreover, because the drug delivery devices can be used and evaluated for a sufficient period of time during clinical trial, which provides plenty opportunities to collect detailed information about the human factor and usability information of the devices. It also provides opportunities to make human factor and usability related improvements based on real use needs, such like button force, surface texture for grabbing.

It is an object of the present invention to provide an improved method to develop parenteral therapeutic product with delivery device throughout clinical trial period.

It is also an object of the present invention to provide a clinical trial method with better blinding and randomization.

It is also an object of the present invention to provide a method for manufacturing clinical trial materials in a cheaper and more efficient manner.

It is also an object of the present invention to provide a method for conducting clinical trial with a device easy-to-use.

It is another object of the present invention to provide a method better for drug/device evaluation and improvement.

Further objects and advantages of the present invention will become apparent from the following description of the preferred embodiment.

BRIEF DESCRIPTION OF THE DRAWINGS

The figures are schematic and simplied for clarity, and they just show details, which are essential to the understanding of the invention, while other details are left out. Throughout, the same reference numerals are used for identical or corresponding parts. Some embodiments are illustrated by way of example and not limitation in the figures of the accompanying drawings in which.

DETAILED DESCRIPTION OF THE INVENTION

The present invention will become more fully understood from the detailed description given hereinbelow and the accompanying drawings which are given by way of illustration only, and thus, are not limitive of the present invention, and wherein:

The methods and apparatus presented herein can be used for conducting clinical trial to develop any of a variety suitable therapeutic agents or substances, such as a drug, into a patient. Initially it may be convenient to define that, the term "variable dose drug delivery device" is meant to a drug delivery device capable of delivering at least two different doses; the term "fixed dose drug delivery device" is meant to a drug delivery device capable of delivering only one dose. The term "autoinjector" is meant to a device automatically delivering total dose within a short period of time, for example, less than 30 second. During the entire drug delivery period, user of the "autoinjector" is required to use hand to keep holding the device in place. The term "infusor" is meant to a device automatically delivering total dose within a long period of time, for example, more than 30 second. During the entire drug delivery period, user of the "infusor" is not required to use hand to keep holding the device in place all the time. The term "fluid" refers to either liquid or suspension. For the drawings, the term "distal end" of a drug delivery device refers to the end of the needle inserted into the patient; the words "upper", "lower", "right" and "left" designate directions in the drawings to which reference is made; the words "inward" and "outward" refer to directions toward and away from, respectively.

Figure 1:
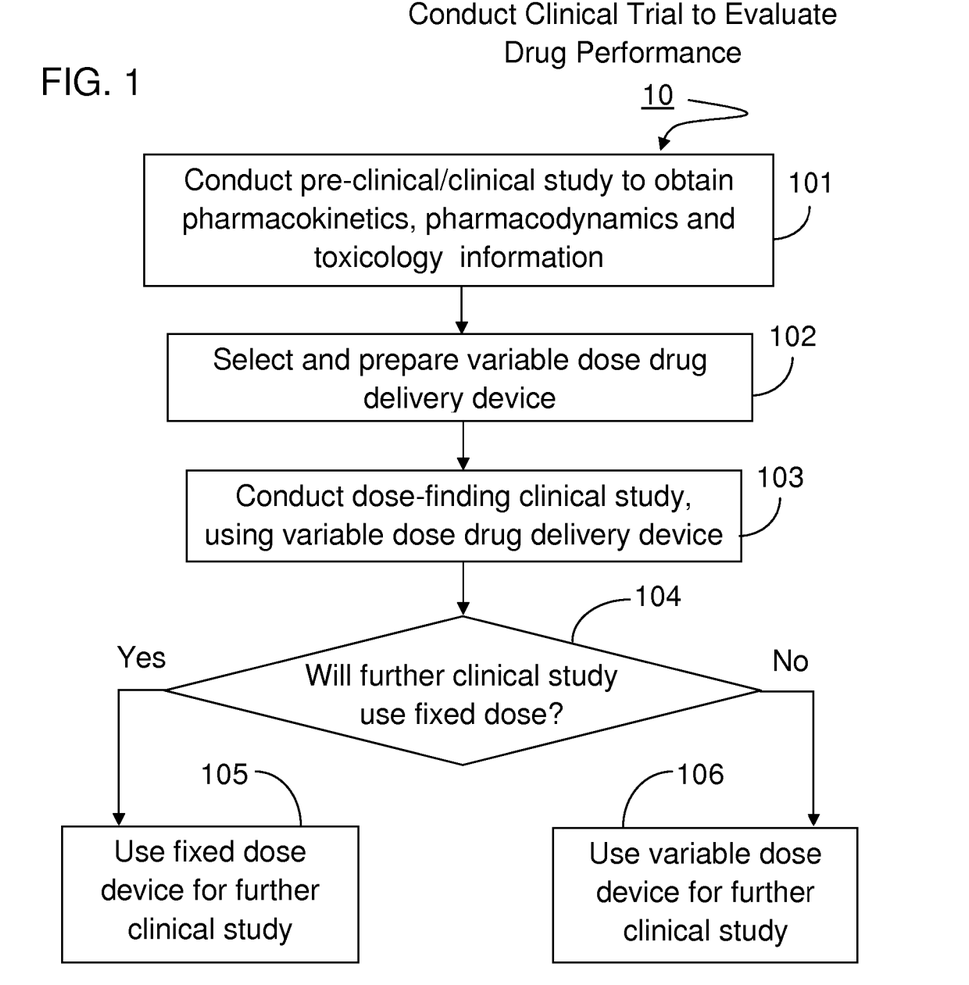
FIG. 1 illustrates a flowchart of an example method of conducting a clinical trial to evaluate drug performance, using dose variable drug delivery device.

FIG. 1 illustrates a block diagram of an example clinical trial method 10 configured to design and run at least one clinical trial. For brevity and conciseness, the following description will describe the execution of an example clinical trial to evaluate drug therapeutic performance. It should be noted that multiple clinical trials can be designed and executed, whether contemporaneously or sequentially, in a similar fashion described hereinafter.

Figure 2:
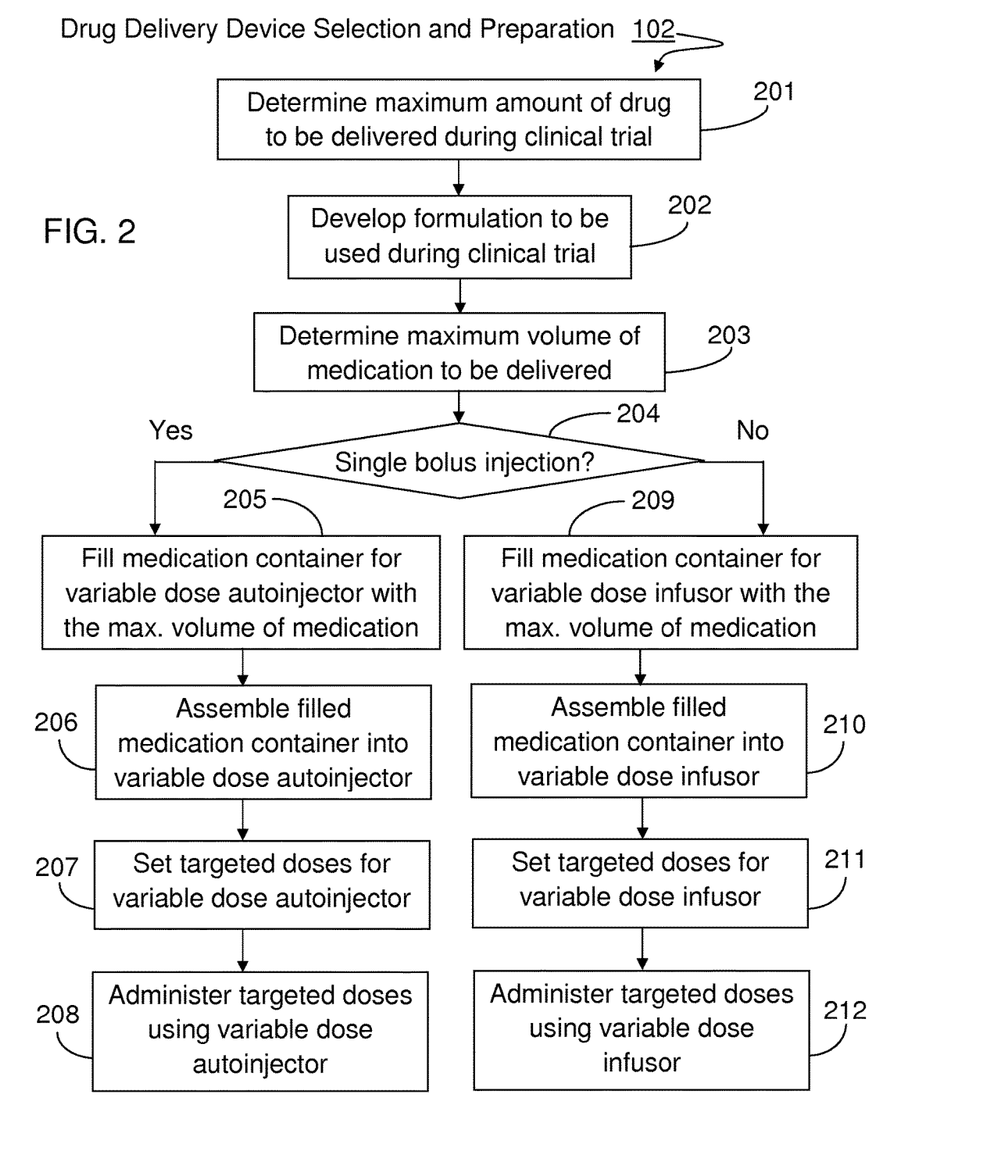
FIG. 2 illustrates a flowchart of an example method of selecting a drug delivery device in accordance with FIG. 1.

The method 10 starts with operation 101 where drug developer conducts pre-clinical studies in animal models and phase I clinical studies in human subjects to obtain pharmacokinetics, pharmacodynamics and toxicology information. At operation 102, a variable dose drug delivery device, which will be used in clinical trial, is selected and prepared. More details about operation 102 is illustrated in FIG. 2. Based on the information collected at operation 101, in drug development, finding an optimal dose (dose-finding study) is normally carried out by a phase II clinical trial, which is represented at operation 103. At operation 103, the dose-finding clinical study is conducted using a variable dose drug delivery device. The variable dose drug delivery device can be variable dose autoinjector or variable dose infusor. Examples of these drug delivery devices are illustrated and explained with reference to FIG. 4-19. Each different dose in the dose-finding clinical trial can be pre-set, through the dose-setting mechanism within the variable dose drug delivery device, during the clinical trial materials manufacturing and preparation. Meantime, the drug formulation and filling volume in the medication container will be the same for all the different doses. By this way, the clinical trial materials manufacturing cost can be greatly reduced and the clinical trial materials manufacturing efficiency can be greatly increased. With using the clinical trial version of the variable dose drug delivery device, the difference in multiple doses in the dose-finding studies is blinded to the participants in the clinical trial. After the dose-finding clinical study, a decision will be made about the dose(s) to be used for further clinical study (for example, phase III clinical study) and final product, at operation 104. If the further clinical study will use fixed dose format, a fixed dose drug delivery device can be utilized to deliver medication, shown as operation 105. The fixed dose drug delivery device has the same external shape and operation mechanisms as the variable dose drug delivery device. More detailed information about transforming the variable dose drug delivery device to the fixed dose drug delivery device is presented in later part of this description. If the further clinical study will use variable dose format, the variable dose drug delivery device can be used continually, shown as operation 106. In the further clinical study, for example, a phase III clinical trial, the selected dose format will be used to demonstrate drug efficacy and safety.

FIG. 2 illustrates a block diagram of an example operation 102 for selecting and preparing drug delivery device to be used in clinical trial studies in detail, according to this invention. The operation for selecting and preparing drug delivery device starts with operation 201 where product developer needs to first determine maximum amount of drug (highest dose of drug substance) to be delivered during clinical trials. This determination can be made based on the toxicology information and efficacy of the drug under development. At operation 202, the product developer will develop one or more appropriate fluid formulations for clinical study. At operation 203, with knowing the maximum amount of drug and the formulation to be used, maximum volume of the medication to be delivered is determined. Then, at operation 204, a decision needs to be made about whether the delivery will be a single bolus injection or an infusion, based on the patient's age, delivery site and the maximum volume of the medication to be delivered for clinical trial evaluation. For example, the maximum amount of medicine that is allowed to be delivered as a single bolus injection in thigh (vastus lateralis muscle) is 4 ml. If the maximum volume of the medication to be delivered for clinical trial evaluation is less than the maximum volume of the medication that can be delivered as single bolus injection at certain tissue site (4 ml for thigh), a variable dose autoinjector is selected for clinical trial studies. To prepare the variable dose autoinjector device, at operation 205, the maximum volume of the medication (less than 4 ml for thigh) to be delivered for clinical trial evaluation is first filled into a pre-filled medication container. It is worth noting that the clinical trial materials manufacturer also needs to consider the size of medication container available for filling the medication when making the selection about autoinjector versus infusor device. At operation 206, the filled medication container is assembled into a variable dose autoinjector. Then, at operation 207, targeted dose(s) are set for clinical trial studies, using the variable dose autoinjector dose-setting mechanism. Further, the variable dose autoinjector is used to administrate clinical trial dose(s), at operation 208. If the maximum volume of the medication to be delivered for clinical trial evaluation is more than the maximum volume of the medication that can be delivered as single bolus injection at certain tissue site (4 ml for thigh), a variable dose infusor is selected for clinical trial studies. Operations 209-212 illustrate the preparation of the variable dose infusor, which is the same as operations used for the preparation of the variable dose autoinjector.

Figure 3:
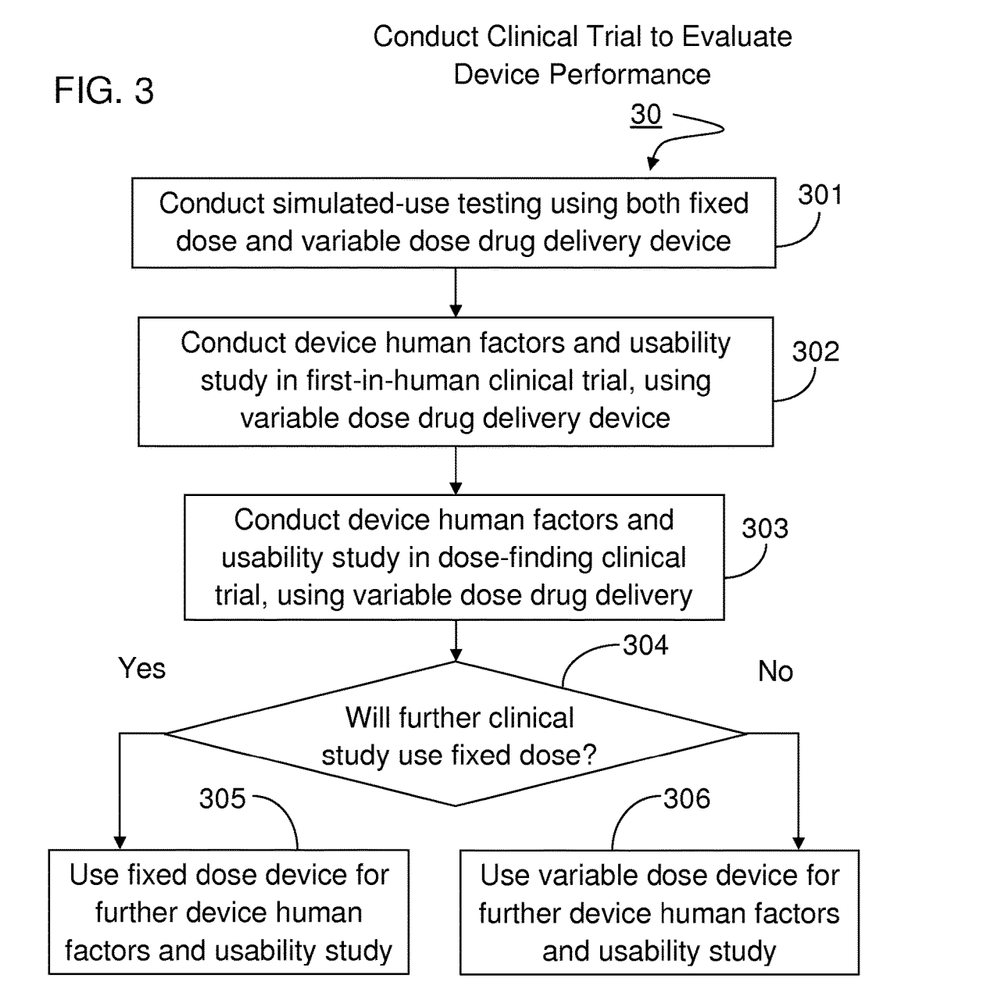
FIG. 3 illustrates a flowchart of an example method of conducting a clinical trial to evaluate device performance, using dose variable drug delivery device.

FIG. 3 illustrates a block diagram of an example clinical trial method 30 configured to evaluate human factors and device usability during clinical trial. The method 30 starts with operation 301 where product developer conducts simulated-use testing to ensure that the device is sufficiently well designed to be safe in actual use. After ensure both a fixed dose drug delivery device and a variable dose drug delivery device are safe in actual use, at operation 302, the variable dose autoinjector is used in first-in-human clinical trial to deliver a safe dose. Then, at operation 303, during dose-finding study, which is normally in Phase II clinical trial, the variable dose autoinjector can be evaluated for delivering multiple different doses to ensure that the delivery device meets human factor and usability requirement across the entire dosing range. The variable dose drug delivery device can be a variable dose autoinjector or a variable dose infusor.

The examples of these drug delivery devices are illustrated and explained in FIG. 4-19. Each dose in the dose-finding clinical trial can be pre-set, through the dose-setting mechanism within the variable dose drug delivery device, during the clinical trial materials manufacturing and preparation. After the dose-finding clinical studies, a decision will be made about the dose(s) to be used for further clinical study (for example, phase III clinical study) and final product, at operation 304. If the further clinical study will use fixed dose format, the fixed dose drug delivery device can be used to deliver medication, shown as operation 305. The fixed dose drug delivery device has the same external shape and operation mechanisms as the variable dose drug delivery device in order to keep most device user interfaces the same. More detailed information about transforming the variable dose drug delivery device to the fixed dose drug delivery device is presented in later part of this description. If the further clinical study will use variable dose format, the variable dose drug delivery device can be used continually, shown as operation 306. In the further clinical study, for example, a phase III clinical trial, the selected device format will be evaluated to demonstrate safety and usability. Through the whole process, clinical trial participants will have opportunity to use the device independently and in as natural a manner as possible, without guidance, coaching, praise or critique from the test facilitator or moderator.

Figure 4:
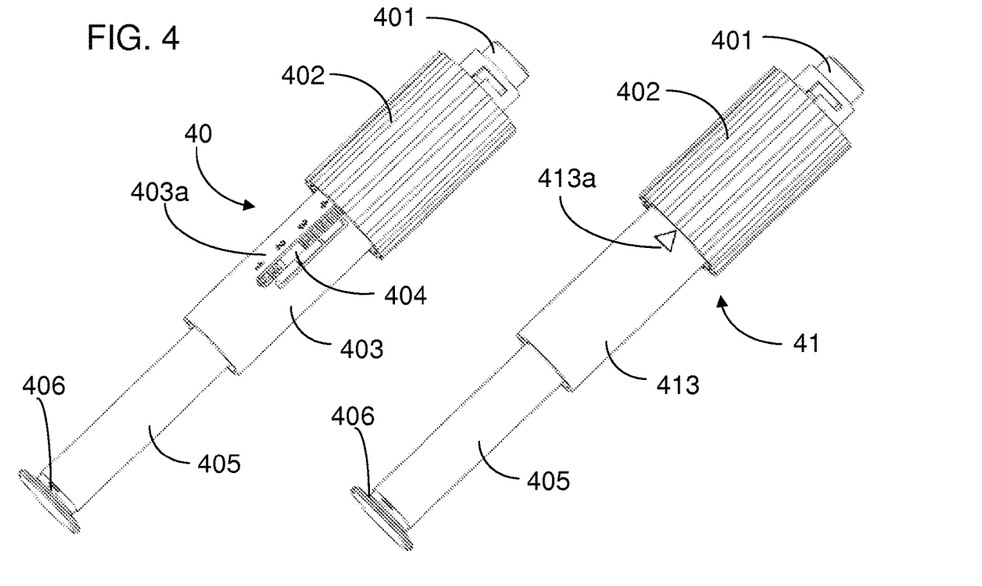
FIG. 4-7 illustrate an example variable dose autoinjector device.
Figure 5:
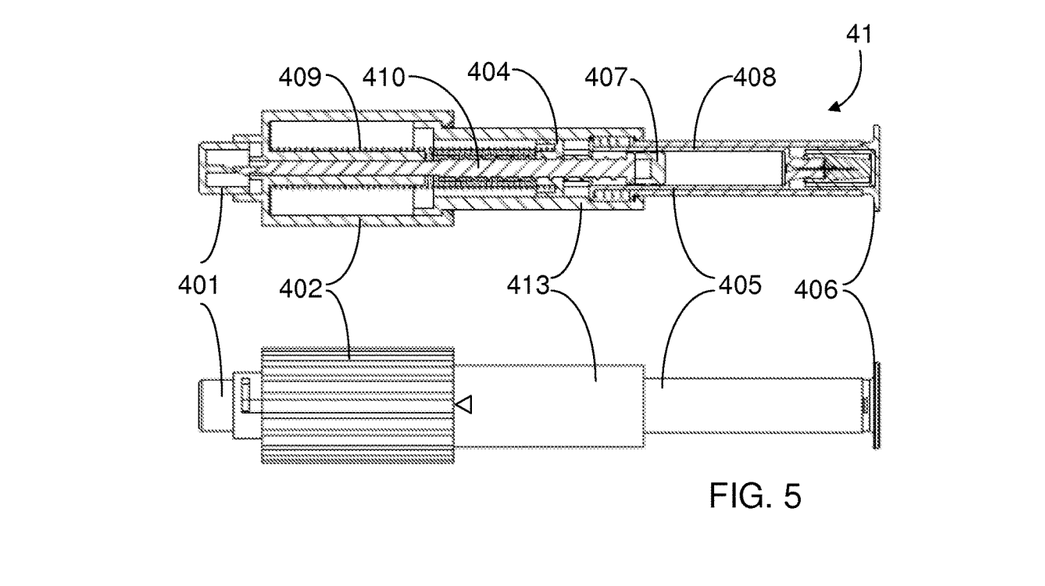
Figure 6:
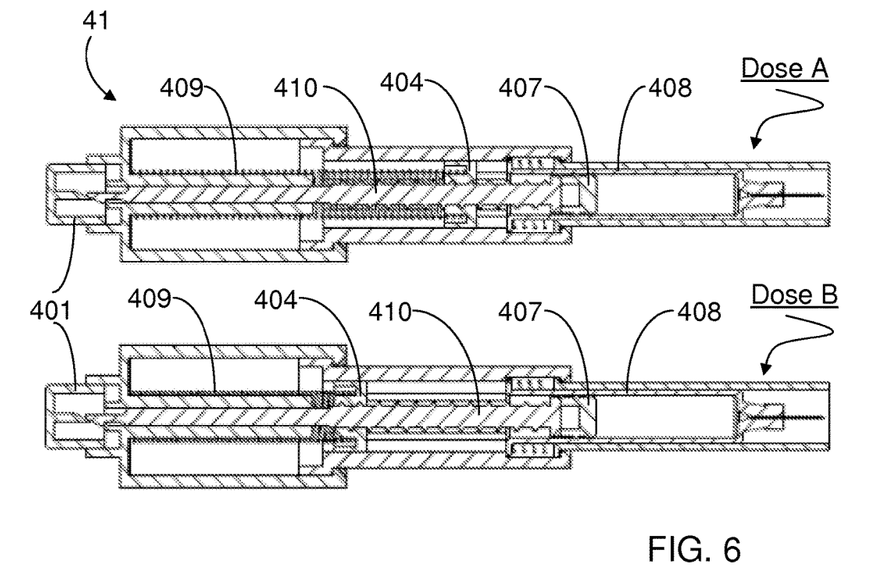
Figure 7:
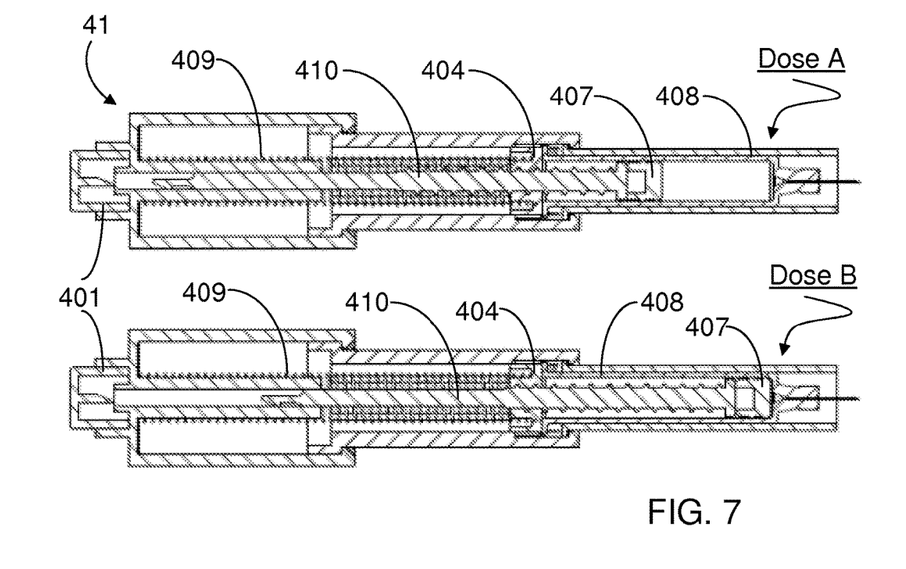
Figure 8:
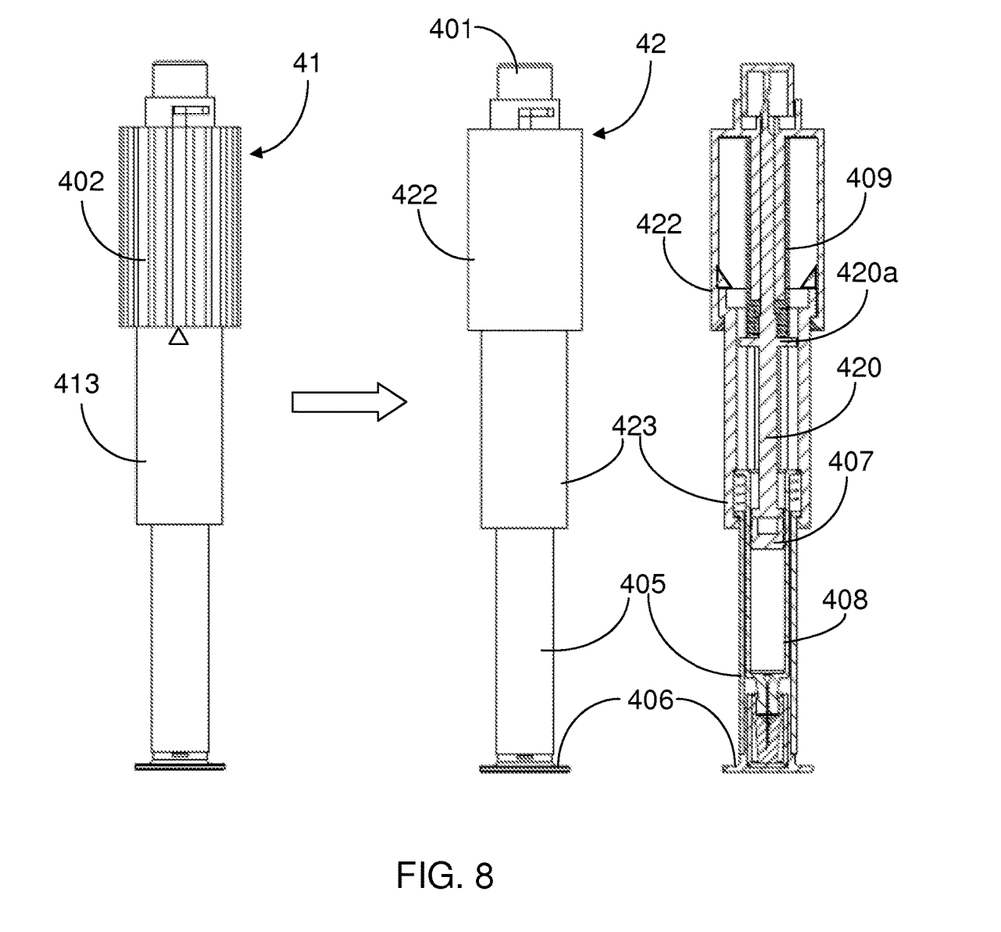
FIG. 8 illustrates an example method of transforming a variable dose autoinjector device to a fixed dose autoinjector device.

FIGS. 4-7 illustrate an example variable dose autoinjector device used in clinical trial according to the invention. With reference to FIG. 4, the variable dose autoinjector 40 has a dose-setting window 403a being defined on a scale cylinder 403, while, in the clinical trial autoinjector device 41, the dose-setting window feature is removed so that the participants in the clinical trial are blinded to the different doses used in the dose-finding study. An optional indicator feature 413a is used to help clinical trial materials manufacturers to set dose. Other than the difference in the scale cylinder components, both autoinjector device 40 and 41 have all the same components and design structures. Therefore, all the device human factors and usability study results obtained from using the variable dose autoinjector device 41 can be implemented to the variable dose autoinjector device 40 if the final product is variable dose. In the variable dose autoinjector device 41, a pre-filled syringe 408 is used as medication container. A push cap 401 is used to activate an automatic injection. The push cap 401 is engaged with a dialing cylinder 402. The dialing cylinder 402 is rotated to set different injection doses used in clinical trial. With reference to FIG. 6, user sets the location of a stopping ring 404 in order to get the different injection doses, for example, Dose A and Dose B. Meantime, before injection, the variable dose autoinjector device 41 is shown with a push rod 410 in a locked state, against biasing force of a driving spring 409. The design of the driving spring 409 can be optimized in order to minimize the difference in injection time when delivering different amount of medication. With reference to FIG. 7, during injection, the push cap 401 is pushed toward to the distal end of the device and the push rod 410 is released and the driving spring 409 drives the stopping ring 404 together with the push rod 410 to move toward the distal end of the automatic medication delivery device 40. A piston 407 is pushed distally. Consequently, fluid medication in the pre-filled syringe 408 is injected from the device into tissue. In order to further enhance the blinding effect, a pre-determined time, for example, 20 second, can be implemented for user to keep the device in place, when delivering the different doses during the clinical trial. More detailed operational information about the injection devices 40, 41 and 42 is disclosed in PCT/US15/47477, Which is incorporated herein by reference. FIG. 8 shows the transformation of the variable dose autoinjector 41, used in clinical trial, into a fixed dose autoinjector 42. After the dose-finding studies in clinical trial, if the final product will be fixed dose, the fixed dose autoinjector 42 can be used to deliver medication. After the dose-setting mechanism is removed, the fixed dose autoinjector 42 has the same external shape and rest of operation mechanisms as the variable dose autoinjector 41 in order to keep most device user interfaces the same. Therefore, all the device human factors and usability study results obtained from using the variable dose autoinjector device 41 can be implemented to the fixed dose autoinjector device 42 if the final product is fixed dose. With reference to FIG. 8, in the fixed dose autoinjector 42, desired amount of medication will be filled into the pre-filled syringe 408 and a cylinder component 422 (representing the dialing cylinder 402 in the variable dose autoinjector 41) is assembled together with the lower cylinder component 423 (representing the lower cylinder 413 in the variable dose autoinjector 41), without rotation mechanism. Moreover, a push rod 420 with an integrated feature 420a is utilized to replace the combination of the push rod 410 and the stopping ring 404 in the variable dose autoinjector 41, for delivering a single fixed dose.

Figure 9:
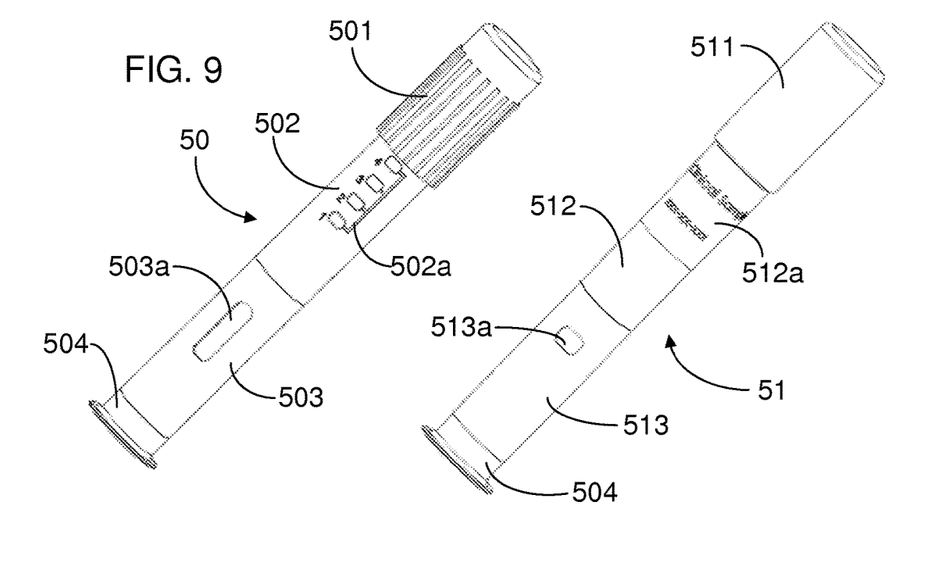
FIG. 9-12 illustrate another example variable dose autoinjector device.
Figure 10:
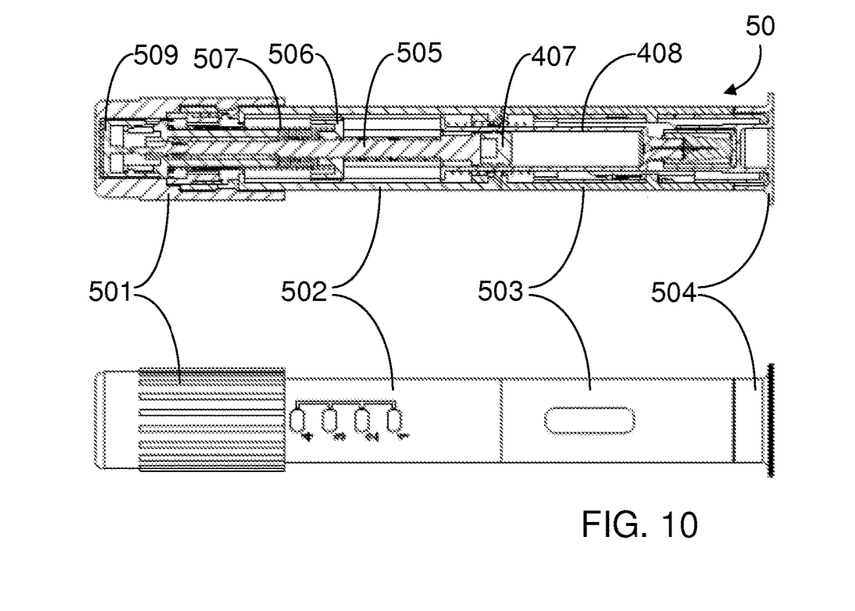
Figure 11:
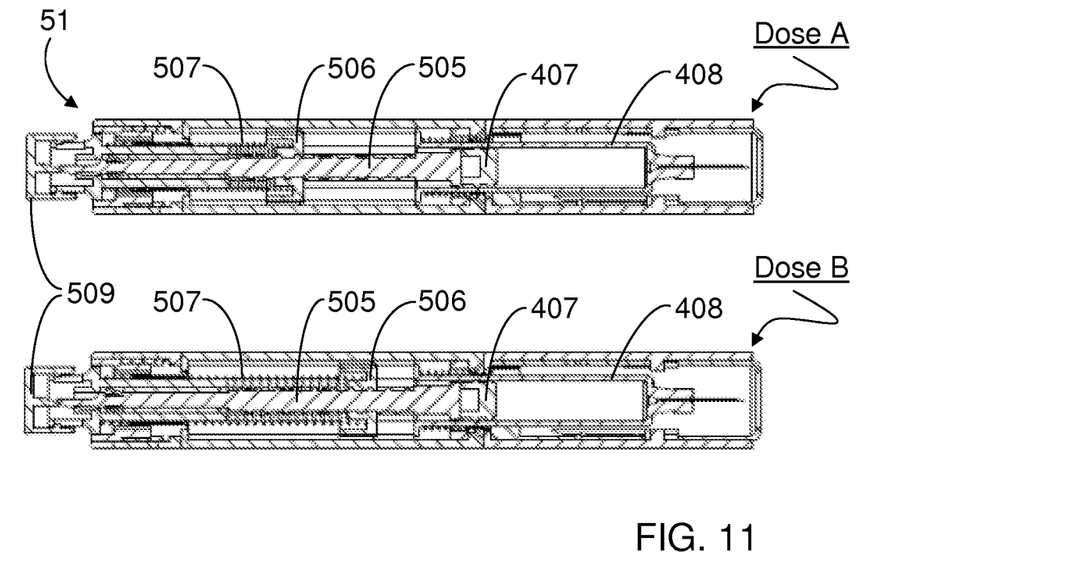
Figure 12:
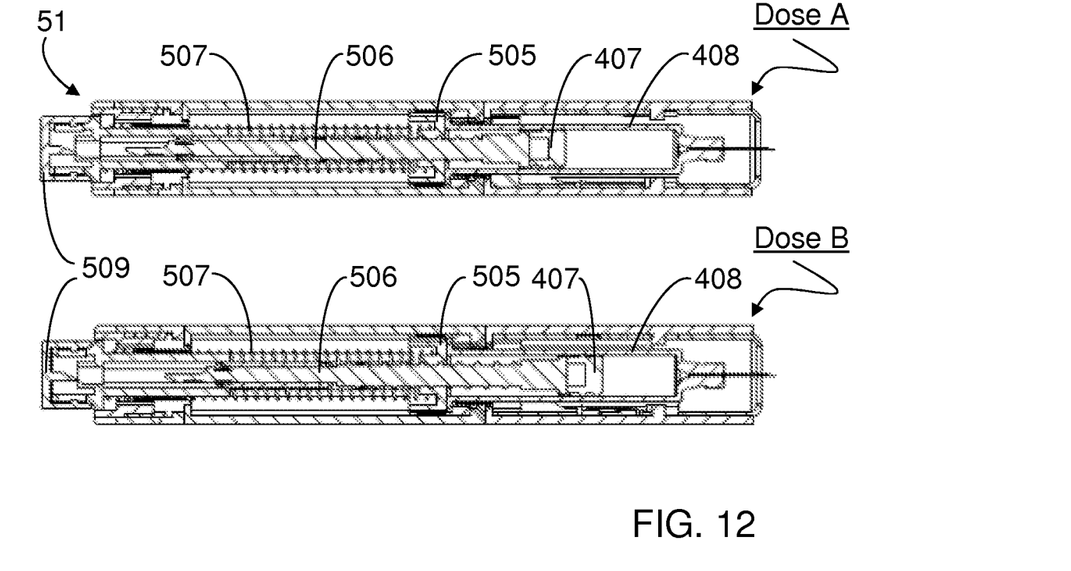
Figure 13:
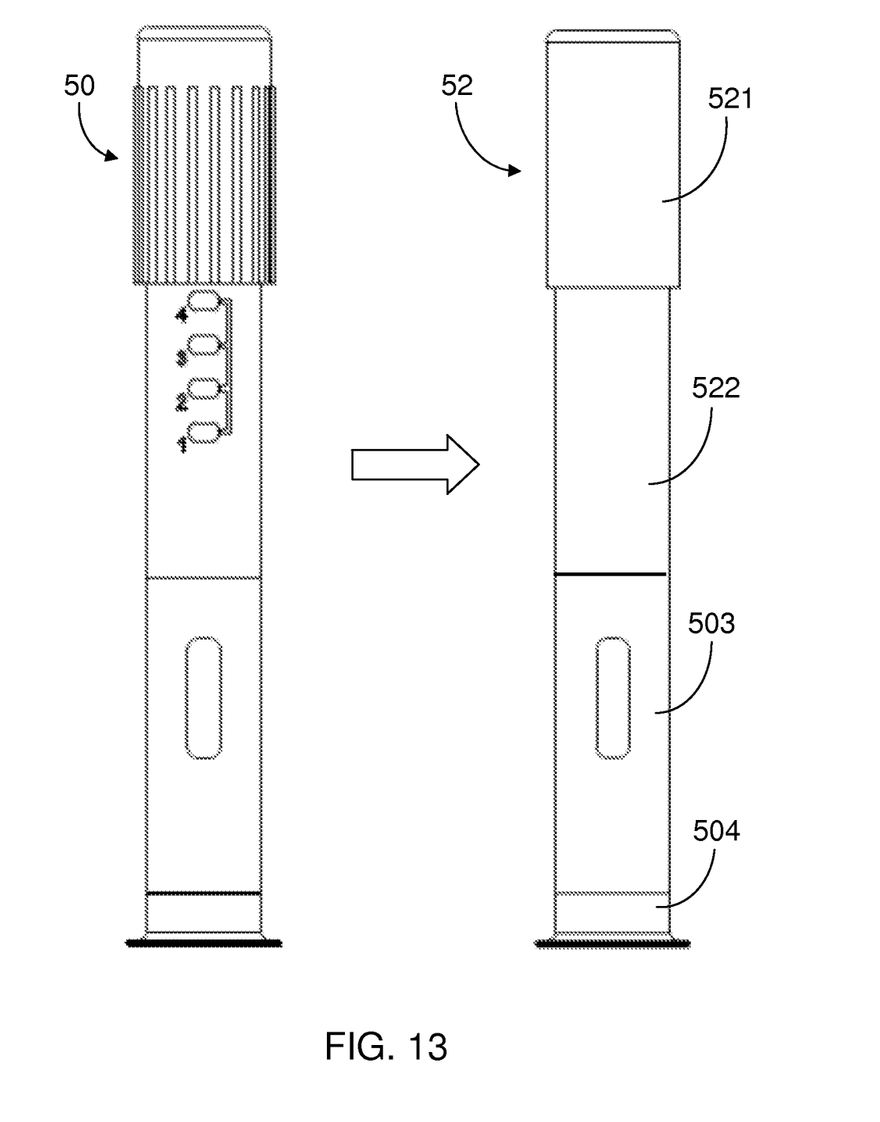
FIG. 13 illustrates another example method of transforming a variable dose autoinjector device to a fixed dose autoinjector device.
Figure 14:
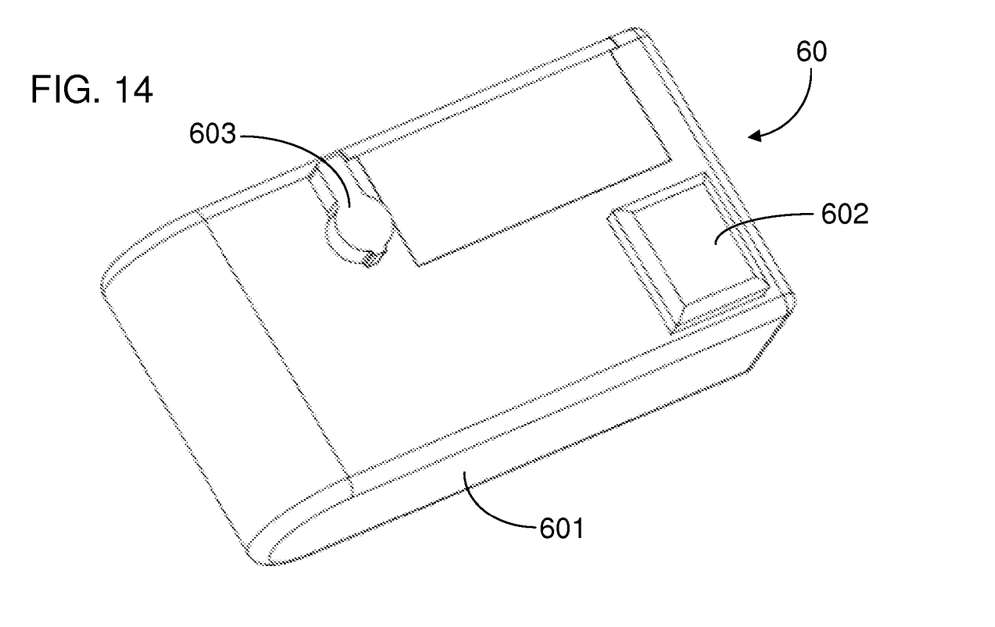
FIG. 14-17 illustrate an example variable dose infusor device.
Figure 15:
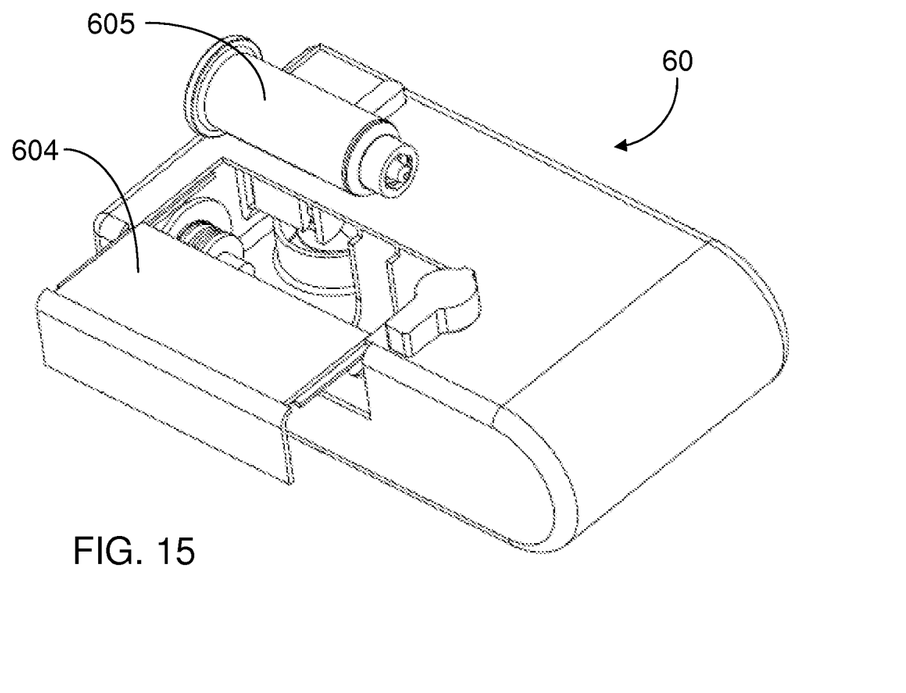

FIGS. 9-12 illustrate another example variable dose autoinjector device used in clinical trial according to the invention. With reference to FIG. 9, the variable dose autoinjector 50 has a dose-setting window 502a being defined on a scale cylinder 502, while, in the clinical trial autoinjector device 51, the dose-setting window feature is covered by a label 512a so that the participants in the clinical trial are blinded to the different doses used in the dose-finding study. Meantime, the viewing window feature 513a on a lower cylinder 513 of the autoinjector device 513 has smaller size than the viewing window feature 530a on a lower cylinder 503 on the autoinjector device 503. Other than the two differences in scale cylinder and lower cylinder, both autoinjector device 50 and 51 have all the same components and design structures. Therefore, all the device human factors and usability study results obtained from using the variable dose autoinjector device 51 can be implemented to the variable dose autoinjector device 50 if the final product is variable dose. With reference to FIG. 10, in the variable dose autoinjector device 50, a pre-filled syringe 408 is used as medication container. A dialing cap 501 is used to set the injection dose. A push cap 509 is used to activate an automatic injection. Before use, the dialing cap 501 is rotated to set the injection dose. After the dose-setting, the clinical trial materials manufacturer replaces the dialing cap 501 with cap component 511 for the clinical trial version of the variable dose autoinjector. By this way, the pre-set dose will not be changed after manufacturing, In clinical study, user removes the cap component 511 and exposes the push cap 509. With reference to FIG. 11, user sets the location of a stopping ring 505 along a push rod 506 in order to get the different injection doses, for example, Dose A and Dose B. Meantime, before injection, the variable dose autoinjector device 51 is shown with the push rod 506 in a locked state, against biasing force of a driving spring 507. With reference to FIG. 12, during injection, the push cap 509 is pushed toward to the distal end of the device 51. The push rod 506 is released and the driving spring 507 drives the stopping ring 505 together with the push rod 506 to move toward the distal end of the device 51. Consequently, the fluid medication in the pre-filled syringe 408 is injected from the device into tissue. More detailed operational information about the injection devices 50, 51 and 52 is disclosed in PCT/US15/47477, Which is incorporated herein by reference. FIG. 13 shows the transformation of the variable dose autoinjector 50 into a fixed dose autoinjector 52, which is similar to the transformation of the variable dose autoinjector 41 to the fixed dose autoinjector 42. After the dose-finding studies in clinical trial, if the final product will be the fixed dose, the fixed dose autoinjector 52 can be used to deliver medication. After the dose-setting mechanism is removed, the fixed dose autoinjector 52 has the same external shape and operation mechanisms as the variable dose autoinjector 50 in order to keep most device user interfaces the same.

Figure 16:
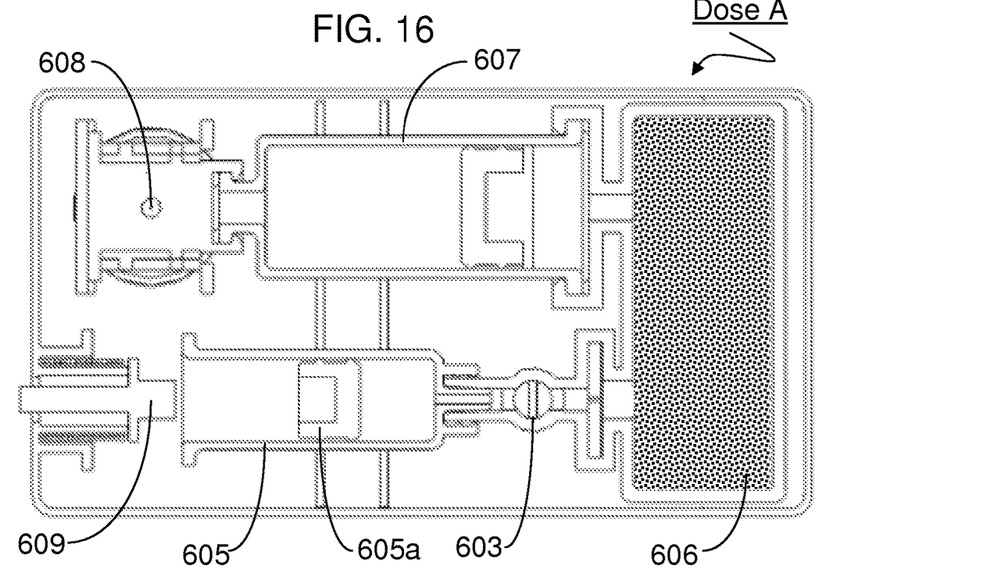
Figure 17:
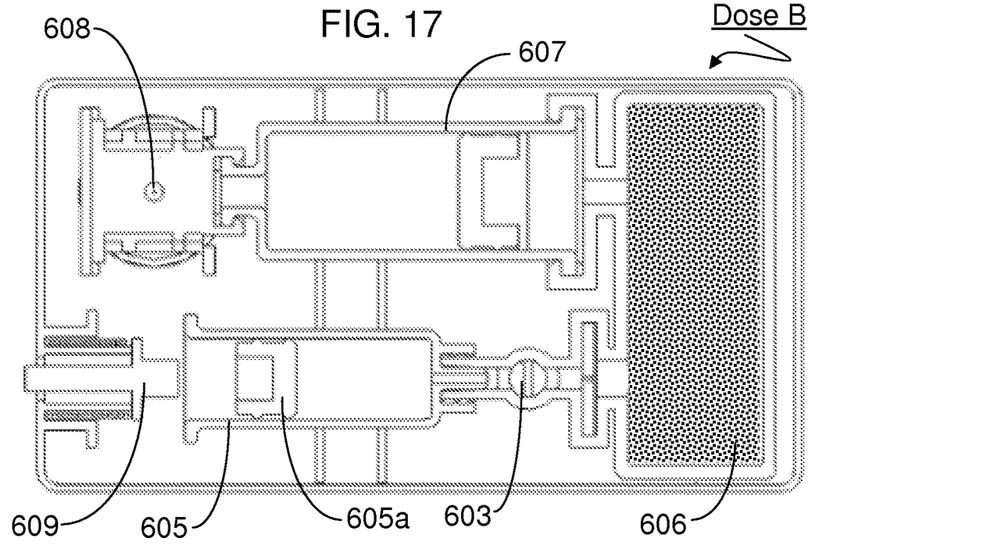

FIGS. 14-17 illustrate the construction and function mechanism of an example variable dose infusor 60 according to the invention. With reference to FIGS. 14-17, the example infusor 60 has major components including a housing 601, a fluid control switch 603, a pre-filled medication container 607, a driver 609, a water container 605, an osmotic driving mechanism 606 and a needle insertion mechanism 602. With reference to FIGS. 16 and 17, the water container 607 contains water and the water content is sealed by a movable piston 605a. For different infusion dose, for example, Dose A and Dose B, different water content is used. The fluid control switch 603 controls the water flowing from the water container 605 into the osmotic chamber 606. The osmotic driving mechanism 606 contains osmotic reagent. The medication container 607 contains fluid medication. When the device is activated, the water in water container 605 flows into the osmotic driving mechanism 606 from the water container 607. Then, osmotic reagent swells and pushes the fluid medication out of the medication container 607, and the fluid medication is delivered through an infusion needle 608. The amount of medication infused can be controlled by the amount of water in the water container 605. Once a housing window 604 is closed, participants in the clinical trials will be blinded to the dose difference. In order to further enhance the blinding effect, a pre-determined time, for example, 20 minutes, can be implemented for user to keep the device in place, when delivering the different doses during the clinical trial. Also, the infusion rate for the device 60 can be optimized for different doses by changing the composition of the osmotic driving mechanism so that the similar infusion time can be achieved. More detailed operational information of the infusion device 60 is disclosed in PCT/US15/35015, Which is incorporated herein by reference. To transform the variable dose infusor device 60 into a fixed dose infusor device, desired amount of medication will be filled into the medication container 607 and a pre-filled water container with fixed amount of water will be used. And, the pre-filled water container with fixed amount of water can be integrated into the infusor device so that the amount of water in the water container can't be changed after the device is manufactured.

Figure 18:
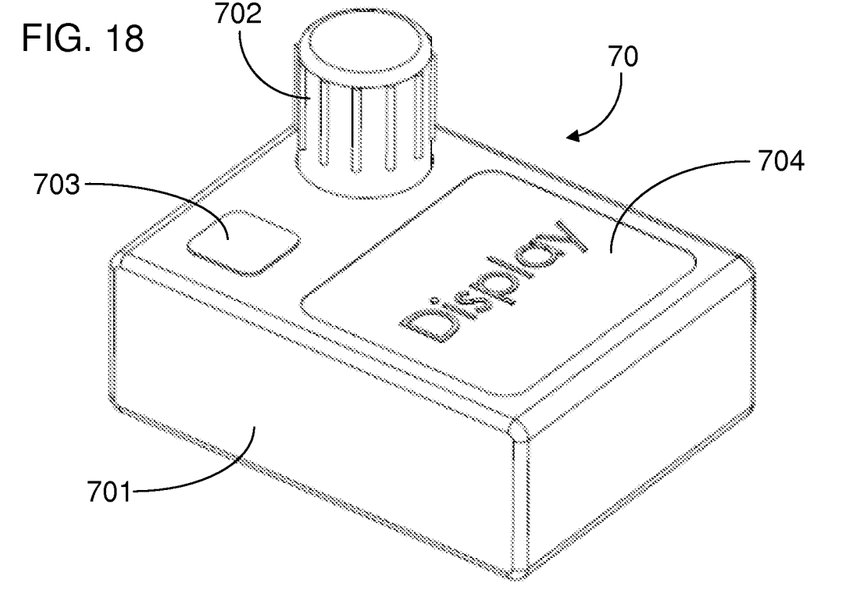
FIG. 18-19 illustrate another example variable dose infusor device.
Figure 19:
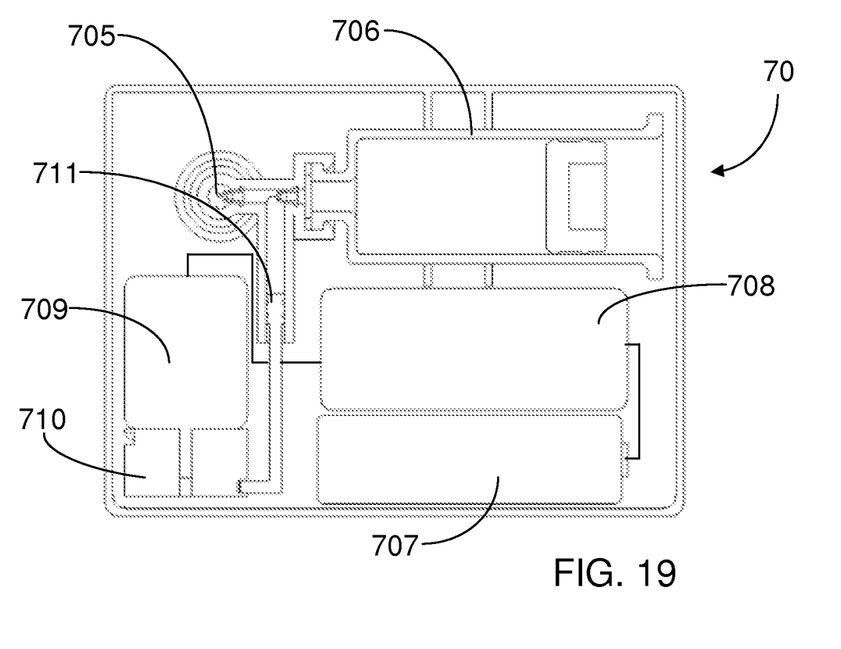

FIG. 18-19 illustrate another example variable dose infusor 70 according to the invention. Major components of the infusor 70 including a housing 701, a medication container 706, an information display panel 704, a power button 703, a reciprocating pump sub-assembly 711, a cam 710, a cam driving motor 709, a microcontroller 708, a battery power supply 707 and a needle insertion mechanism 702. With reference to FIG. 19, the movement of the reciprocating pump sub-assembly 711 is controlled by the rotational movement of the cam 710. The rotational movement of the cam 710 is driven by the cam driving motor 709. The micorcontroller 708 controls the rotation speed and duration of the cam 710 through the cam driving motor 709. The fluid medication in the medication container 706 is delivered through an infusion needle 705. The target infusion dose and infusion rate can be set by inputting instruction on the information display panel 704. During the clinical trial, the information on the display panel 704 can be hidden for blinding purpose. A pre-determined infusion time, for example, 20 minutes, can be implemented for all the different doses during the clinical trial, in order to further enhance the blinding effect. Also, the infusion rate for the device 70 can be changed for different doses by changing the control program on the microcontroller 708 so that the similar or same infusion time can be achieved for different doses. More detailed operational information of the infusor 70 is disclosed in PCT/US15/35015, Which is incorporated herein by reference. To transform the variable dose infusor 70 into a fixed dose infusor device, desired amount of medication will be filled into the medication container 706 and a program will be pre-set for delivering fixed dose, through the micorcontroller 708.

All the steps and features in the above embodiments and concepts herein can be inter-changed and combined to generate new method. Those of skill in the art will understand that modifications (additions and/or removals) of various steps of the methods, components of the apparatuses, and/or systems and embodiments described herein may be made without departing from the full scope and spirit of the present invention, which encompass such modifications and any and all equivalents thereof.

The invention claimed is:

1. A method of conducting a blind clinical trial for delivering a parenteral therapeutic product with at least a first and second variable dose autoinjector device, the method comprising:

generating a toxicology profile for the parenteral therapeutic product through a preclinical animal study;

calculating a maximum dose of the parenteral therapeutic product for the blind clinical trial based on the toxicology profile;

producing the first and second variable dose autoinjector devices each having a dose-setting window and a dose setting mechanism;

loading the maximum dose of the parenteral therapeutic product into each of the first and second variable dose autoinjector devices;

adjusting the dose setting mechanism on the first variable dose autoinjector device to set a first clinical trial dose and adjusting the dose setting mechanism on the second variable dose autoinjector device to set a second clinical trial dose, wherein the first and second clinical trial doses are different from each other and lower than the maximum dose;

after adjusting the clinical trial doses, removing a component of the dose setting mechanism on each variable dose autoinjector device so that the set first and second clinical trial doses are not changed after manufacturing;

covering each dose-setting window so that participants in the blind clinical trial are blinded to the set clinical trial doses;

administering the first clinical trial dose with the first variable dose autoinjector device in the blind clinical trial; and administering the second clinical trial dose with the second variable dose autoinjector device in the blind clinical trial.

* * * * *